(12) United States Patent
Nakamura

(10) Patent No.: US 11,553,884 B2
(45) Date of Patent: Jan. 17, 2023

(54) INFORMATION DISPLAY METHOD, INFORMATION DISPLAY DEVICE, INFORMATION DISPLAY SYSTEM, AND COMPUTER-READABLE MEDIUM

(71) Applicant: Satoshi Nakamura, Chiba (JP)

(72) Inventor: Satoshi Nakamura, Chiba (JP)

(73) Assignee: RICOH COMPANY, LTD., Tokyo (JP)

( * ) Notice: Subject to any disclaimer, the term of this patent is extended or adjusted under 35 U.S.C. 154(b) by 323 days.

(21) Appl. No.: 16/811,267

(22) Filed: Mar. 6, 2020

(65) Prior Publication Data

US 2020/0297289 A1 Sep. 24, 2020

(30) Foreign Application Priority Data

Mar. 18, 2019 (JP) .............................. JP2019-049953

(51) Int. Cl.

| | |
|---|---|
| *G06K 9/00* | (2022.01) |
| *A61B 5/08* | (2006.01) |
| *A61B 5/00* | (2006.01) |
| *G06T 7/00* | (2017.01) |
| *A61B 5/24* | (2021.01) |

(52) U.S. Cl.
CPC .............. *A61B 5/742* (2013.01); *A61B 5/24* (2021.01); *G06T 7/0012* (2013.01); *G06T 2207/20036* (2013.01); *G06T 2207/30016* (2013.01)

(58) Field of Classification Search
CPC ............ G06K 9/00; A61B 5/7425; A61B 5/08
USPC ....... 382/100, 103, 106, 128–132, 168, 173, 382/181, 199, 219, 224, 254, 276, 382/286–291, 305; 378/4, 21; 600/425, 600/544
See application file for complete search history.

(56) References Cited

U.S. PATENT DOCUMENTS

2017/0238879 A1\* 8/2017 Ducreux ................ A61B 5/164
2018/0143199 A1\* 5/2018 Liu ........................ G06T 7/0002
(Continued)

FOREIGN PATENT DOCUMENTS

| JP | H07227386 A | 8/1995 |
|---|---|---|
| JP | H10295659 A | 11/1998 |

(Continued)

OTHER PUBLICATIONS

JP Office Action for corresponding Japanese Patent Application No. 2019-049953 dated Sep. 13, 2022.

*Primary Examiner* — Seyed H Azarian
(74) *Attorney, Agent, or Firm* — Harness, Dickey & Pierce, P.L.C.

(57) ABSTRACT

An information display method displays brain activity information calculated using a biological signal measured from a living body so as to be superimposed on a morphological image including a plurality of sectional images. The information display method includes: acquiring mask information representing an area belonging to a brain in the morphological image; and detecting one or more extremal value positions with spatial extremal values in the brain activity information based on the mask information. A sectional image corresponding to the one or more extremal value positions is acquired from the morphological image. A brain activity distribution corresponding to the sectional image is acquired. The brain activity distribution is displayed so as to be superimposed on the sectional image.

20 Claims, 11 Drawing Sheets

(56) References Cited

U.S. PATENT DOCUMENTS

| | | | | |
|---|---|---|---|---|
| 2018/0325483 A1* | 11/2018 | Shinohara | .............. | A61B 6/466 |
| 2019/0236824 A1 | 8/2019 | Shinohara et al. | | |
| 2019/0274640 A1* | 9/2019 | Mukasa | ............... | A61B 5/7425 |
| 2020/0202532 A1* | 6/2020 | Wang | ....................... | G06T 7/155 |

FOREIGN PATENT DOCUMENTS

| | | |
|---|---|---|
| JP | 2005-328933 A | 12/2005 |
| JP | 2018-153612 | 10/2018 |
| JP | 2020-089700 A | 6/2020 |

\* cited by examiner

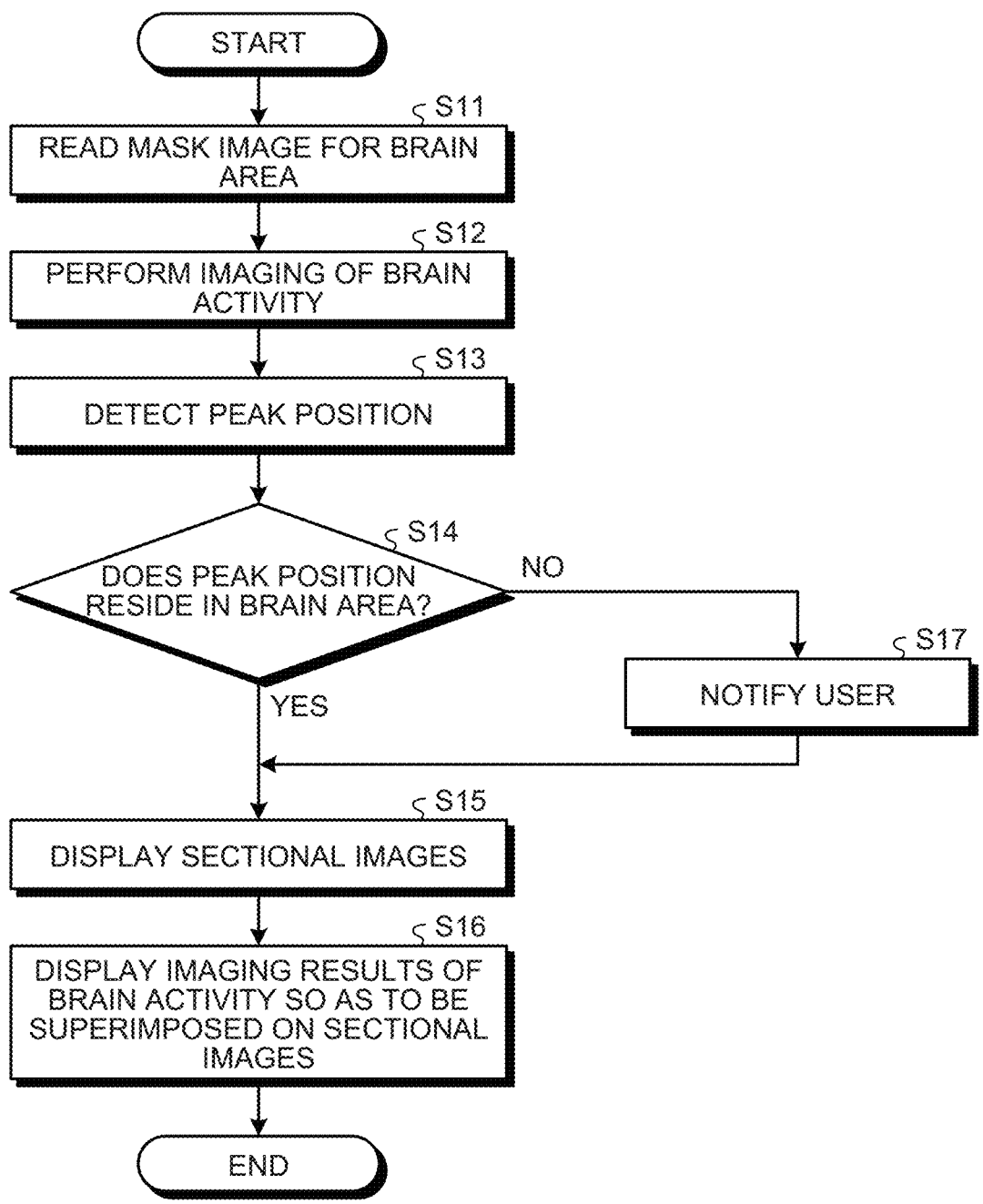

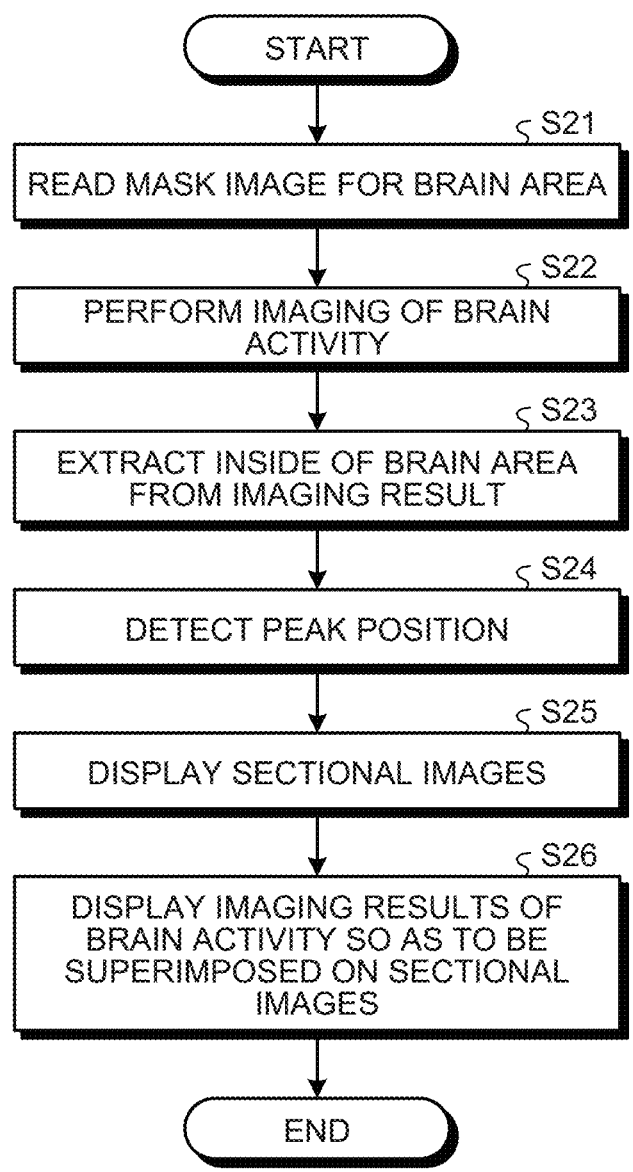

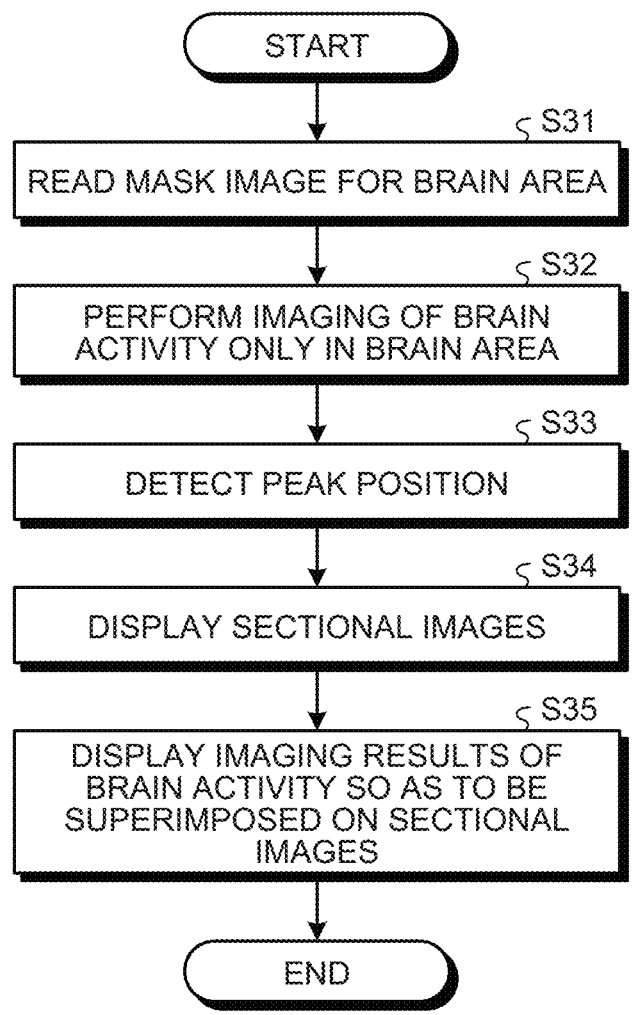

INFORMATION DISPLAY METHOD, INFORMATION DISPLAY DEVICE, INFORMATION DISPLAY SYSTEM, AND COMPUTER-READABLE MEDIUM

CROSS-REFERENCE TO RELATED APPLICATIONS

The present application claims priority under 35 U.S.C. § 119 to Japanese Patent Application No. 2019-049953, filed on Mar. 18, 2019. The contents of which are incorporated herein by reference in their entirety.

BACKGROUND OF THE INVENTION

1. Field of the Invention

The present invention relates to an information display method, an information display device, an information display system, and a computer-readable medium.

2. Description of the Related Art

Efforts are generally made to analyze a brain activity by estimating a spatial intensity distribution of signal sources generating biological signals based on the biological signals measured from a living body using a magnetoencephalograph or an electroencephalograph, and superimposing the result on a morphological image generated by, for example, magnetic resonance imaging (MRI). For example, in a research field called "brain functional mapping", areas responsible for important physical functions are identified by giving a subject a predetermined task or stimulus, and analyzing a change in time or frequency of the brain activity associated therewith. In that operation, a visualization method is used in which the brain activity is superimposed on the morphological image.

However, the brain activity is three-dimensionally distributed, and, in addition, finding a characteristic change in the brain activity on the time axis or the frequency axis requires searching for the target change by trial and error, thus requiring a large amount of labor. In other words, the brain activity provides a large amount of data of four or five dimensions obtained by adding a dimension of time or frequency to the three dimensions representing a space. To cope with the problem described above, a technique called "peak detection" has been conventionally used to automatically detect positions of extremal values (peaks) from the three-dimensional distribution of the brain activity. Conventional techniques are described, for example, in Japanese Unexamined Patent Application Publication No. 2018-153612.

The peak detection is used to analyze the spatial intensity distribution of the estimated signal source. The intensity distribution is, however, generally estimated by simplifying the shape of the brain. Therefore, the distribution does not correctly reflect the shape of the brain. Therefore, the positions (peak positions) obtained by the peak detection may be present outside the brain area. As a result, when sectional images corresponding to the peak positions are detected from the morphological image and displayed, some of the sectional images may not include the brain area, and may cause a user to be unnecessarily confused or have a sense of uncertainty about the estimation result.

The present invention has been made in view of the above, and aims to provide an information display method, an information display device, an information display system, a computer-readable medium that enable appropriate display of the sectional images including the brain area.

SUMMARY OF THE INVENTION

According to an aspect of the present invention, an information display method displays brain activity information calculated using a biological signal measured from a living body so as to be superimposed on a morphological image including a plurality of sectional images. The information display method includes: acquiring mask information representing an area belonging to a brain in the morphological image; and detecting one or more extremal value positions with spatial extremal values in the brain activity information based on the mask information. A sectional image corresponding to the one or more extremal value positions is acquired from the morphological image. A brain activity distribution corresponding to the sectional image is acquired. The brain activity distribution is displayed so as to be superimposed on the sectional image.

BRIEF DESCRIPTION OF THE DRAWINGS

FIG. 10 is a flowchart illustrating an example of a flow of processing to display the peak position so as to be superimposed on the sectional images;

FIG. 11 is a flowchart illustrating an example of a flow of processing to display the peak position so as to be superimposed on the sectional images in a second embodiment of the present invention; and FIG. 12 is a flowchart illustrating an example of a flow of processing to display the peak position so as to be superimposed on the sectional images in a third embodiment of the present invention.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
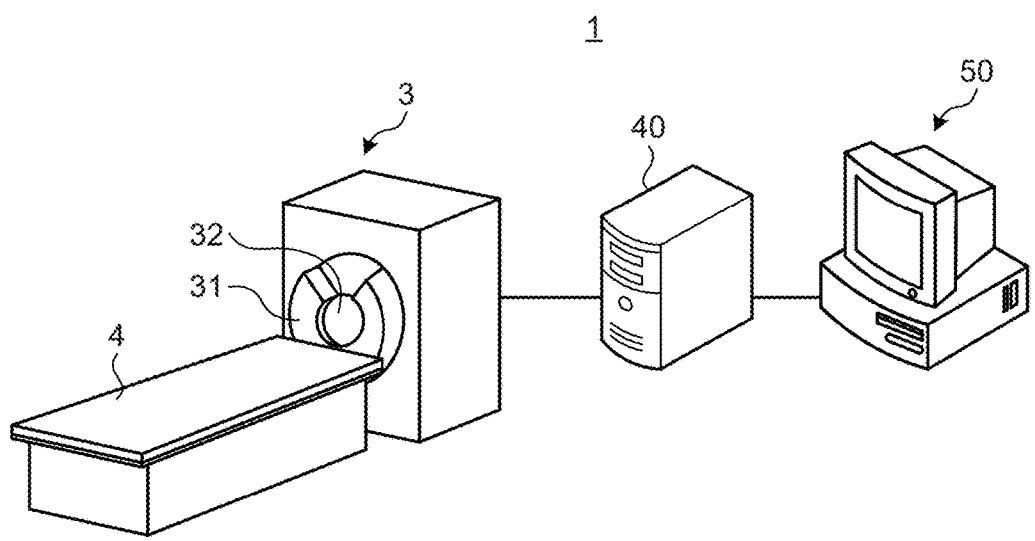
FIG. 1 is a schematic diagram of a biological signal measurement system according to a first embodiment of the present invention.

The terminology used herein is for the purpose of describing particular embodiments only and is not intended to be limiting of the present invention.

As used herein# the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

First Embodiment

The following describes embodiments of an information display method, an information display device, an information display system, a computer-readable medium according to the present invention in detail with reference to the drawings. The present invention is not limited to the following embodiments. Components in the following embodiments include those easily conceivable by those skilled in the art, those substantially the same, and those in the scope of what are called equivalents. Furthermore, the components can be variously omitted, replaced, modified, or combined within the scope not deviating from the gist of the following embodiments.

Schematic Configuration of Biological Signal Measurement System

FIG. 1 is a schematic diagram of a biological signal measurement system according to a first embodiment of the present invention. A schematic configuration of a biological signal measurement system 1 according to the present embodiment will be described using FIG. 1.

The biological signal measurement system 1 is a system that measures and displays a plurality of types of biological signals (for example, magnetoencephalographic (MEG) signals and electroencephalographic (EEG) signals) of a subject. The biological signals serving as measurement objects are not limited to the MEG signals and the EEG signals, and may be other signals related to brain activity. As illustrated in FIG. 1, the biological signal measurement system 1 includes a measuring device 3 that measures one or more biological signals of the subject, a server device 40 that records the biological signals measured by the measuring device 3, and an information processing device 50 that analyzes the biological signals recorded in the server device 40. FIG. 1 illustrates the server device 40 and the information processing device 50 as separate devices. However, for example, at least some functions of the server device 40 may be incorporated in the information processing device 50. The biological signal measurement system 1 is an example of the information display system. The information processing device 50 is an example of the information display device.

In the example of FIG. 1, the subject is laid on a table 4 with electrodes (or sensors) for EEG measurement attached to the head, and the head is placed in a recess 32 of a dewar 31 of the measuring device 3. The dewar 31 is a container under a cryogenic environment using liquid helium, and a number of magnetic sensors for MEG measurement are disposed in the recess 32 of the dewar 31. The measuring device 3 collects the EEG signals from the electrodes and the MEG signals from the magnetic sensors, and outputs data (hereinafter, called "measurement data" in some cases) including the collected EEG signals and MEG signals to the server device 40. The measurement data output to the server device 40 is read, displayed, and analyzed by the information processing device 50. Although the dewar 31 incorporating the magnetic sensors and the table 4 are generally disposed in a magnetic shielding room, the magnetic shielding room is not illustrated in FIG. 1 for convenience of illustration.

The information processing device 50 is a device that displays waveforms of the MEG signals obtained from the magnetic sensors and waveforms of the EEG signals obtained from the electrodes in synchronization with each other on the same time axis. The EEG signals refer to signals that represent electrical activity of neurons (flow of ionic charges occurring at dendrites of neurons during synaptic transmission) as voltage values between the electrodes. The MEG signals refer to signals that represent small electrical field variations caused by electrical activity of the brain. A brain magnetic field is detected by highly sensitive superconducting quantum interference device (SQUID) sensors. The EEG signals and the MEG signals are examples of the "biological signals".

Hardware Configuration of Information Processing Device

Figure 2:
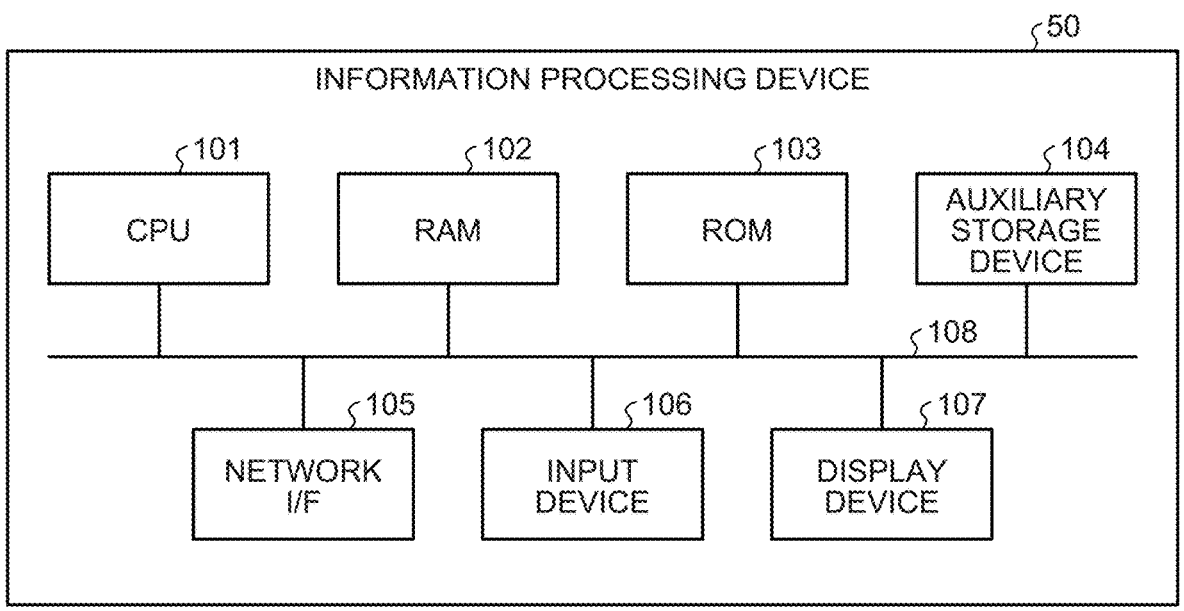
FIG. 2 is a hardware block diagram illustrating an example of a hardware configuration of an information processing device according to the first embodiment.

FIG. 2 is a hardware block diagram illustrating an example of a hardware configuration of the information processing device according to the first embodiment. The hardware configuration of the information processing device 50 according to the present embodiment will be described using FIG. 2.

As illustrated in FIG. 2, the information processing device 50 includes a central processing unit (CPU) 101, a random-access memory (RAM) 102, a read-only memory (ROM) 103, an auxiliary storage device 104, a network interface (I/F) 105, an input device 106, and a display device 107. These hardware components are connected to one another through a bus 108.

The CPU 101 is an arithmetic device that controls overall operations of the information processing device 50, and performs various types of information processing. The CPU 101 executes an information display program stored in the ROM 103 or the auxiliary storage device 104 to control display operations of a measurement collection screen and an analysis screen (for example, a time-frequency analysis screen).

The RAM 102 is a volatile storage device that is used as a work area of the CPU 101, and stores therein main control parameters and information. The ROM 103 is a nonvolatile storage device that stores therein, for example, a basic input-output program. The ROM 103 may store therein, for example, the above-mentioned information display program.

The auxiliary storage device 104 is a storage device, such as a hard disk drive (HDD) or a solid-state drive (SSD). The auxiliary storage device 104 stores therein, for example, a control program to control the operations of the information processing device 50 and various types of data and files required for the operations of the information processing device 50.

The network I/F 105 is a communication interface for communicating with devices such as the server device 40 on a network. The network I/F 105 is implemented by, for example, a network interface card (NIC) conforming to the Transmission Control Protocol/Internet Protocol (TCP/IP).

The input device 106 is a user interface device having input functions, such as a touchscreen panel, a keyboard, a mouse, and operation buttons. The display device 107 is a display device that displays various types of information. The display device 107 is implemented by, for example, a display function of the touchscreen panel, a liquid crystal display (LCD), or organic electroluminescence (EL). The display device 107 displays the measurement collection screen and the analysis screen, and updates the screens according to input-output operations through the input device 106.

The hardware configuration of the information processing device 50 illustrated in FIG. 2 is merely an example, and may include other devices. The information processing device 50 illustrated in FIG. 2 has the hardware configuration assumed as a personal computer (PC). The information processing device 50 is, however, not limited thereto, and may be a mobile terminal such as a tablet computer. In that case, the network I/F 105 only needs to be a communication interface having a wireless communication function.

Functional Configuration of Information Processing Device

Figure 3:
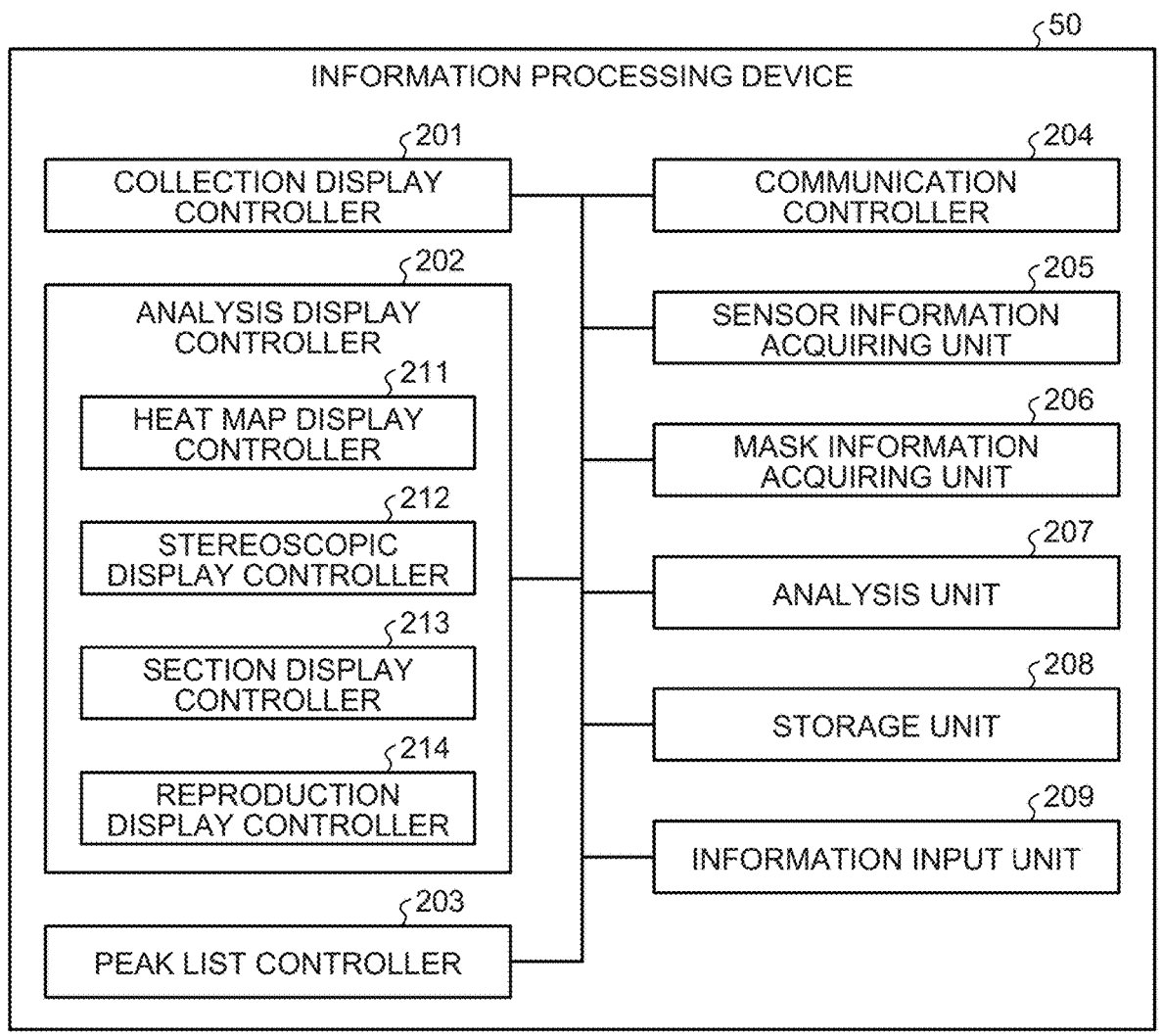
FIG. 3 is a functional block diagram illustrating an example of a functional configuration of the information processing device according to the first embodiment.

FIG. 3 is a functional block diagram illustrating an example of a functional configuration of the information processing device according to the present embodiment. The functional configuration of the information processing device 50 according to the present embodiment will be described using FIG. 3.

As illustrated in FIG. 3, the information processing device 50 includes a collection display controller 201, an analysis display controller 202, a peak list controller 203, a communication controller 204, a sensor information acquiring unit 205, a mask information acquiring unit 206, an analysis unit 207, a storage unit 208, and an information input unit 209.

The collection display controller 201 is a functional unit for controlling screen display during a collection operation of sensor information.

The analysis display controller 202 is a functional unit for controlling screen display of, for example, signal intensities of the biological signals calculated by the analysis unit 207 from the sensor information (EEG signals and MEG signals) acquired by the sensor information acquiring unit 205. The analysis display controller 202 further includes a heat map display controller 211, a stereoscopic display controller 212, a section display controller 213, and a reproduction display controller 214

The heat map display controller 211 is a functional unit for controlling the screen display of a heat map 611 of a time-frequency analysis screen 601 to be described later (refer to FIG. 5). The stereoscopic display controller 212 is a functional unit for controlling the screen display of a stereoscopic view 612 of the time-frequency analysis screen 601. The section display controller 213 is a functional unit for controlling the screen display of a three-sided head view 613 of the time-frequency analysis screen 601. The reproduction display controller 214 is a functional unit for controlling reproduction display according to an operational input to reproduction control panel 615 of the time-frequency analysis screen 601.

The peak list controller 203 detects extremal values (peaks) of the signal intensities satisfying a set condition. The peak list controller 203 is also a functional unit for registering the detected extremal values on a peak list 614 of the time-frequency analysis screen 601.

The following describes a method in which the peak list controller 203 detects the extremal values of the signal intensities. The peak list controller 203 detects positions having spatial extremal values from an imaging result of the brain activity. A spatial extremal value refers to the following state: when focusing on a certain voxel, a value stored in the voxel is greater (maximum) or smaller (minimum) than all the adjacent voxels (in six directions of front, rear, up, down, right, and left, or 26 directions obtained by adding diagonal directions thereto). When a magnitude relation between values of the adjacent voxels is determined, a case may be allowed in which the values are equal. A threshold may be set for the determination of the magnitude relation between values of the adjacent voxels, and a value may be determined to be greater or smaller only when the absolute value of a difference is equal to or greater than the threshold.

The peak list controller 203 may derive a peak cluster size in addition to a peak position. The term "peak cluster" refers to an indicator representing a spread of a peak, and refers to the number of voxels satisfying a predetermined condition that are connected to the voxel in the peak position. The predetermined condition is, for example, that the values of the voxels are equal to or greater than a predetermined threshold when the peak position is the maximum, or that the values of the voxels are equal to or smaller than the predetermined threshold when the peak position is the minimum.

The communication controller 204 is a functional unit for making data communication with, for example, the measuring device 3 or the server device 40. The communication controller 204 is implemented by the network I/F 105 illustrated in FIG. 2.

The sensor information acquiring unit 205 is a functional unit for acquiring the sensor information (EEG signals and MEG signals) from the measuring device 3 or the server device 40 through the communication controller 204.

The mask information acquiring unit 206 acquires a mask image (mask information) for a brain area of the subject. The term "mask image" refers to an image storing information for distinguishing the brain area from other areas in a morphological image (or a sectional image constituting the morphological image) of the brain generated based on the biological signals of the subject measured by the biological signal measurement system 1. The mask image is, for example, a binary image in which pixels belonging to the brain area have a pixel value of 1, and pixels not belonging to the brain. area have a pixel value of 0. The mask image is not limited to the binary image. The format of the image does not matter as long as the brain area can be distinguished from the other areas. Despite the name, the mask image need not take a form of an image, and may be, for example, a list storing coordinate values in the morphological image belonging to the brain area.

The mask image is created by, for example, processing the sectional image constituting the morphological image of the brain of the subject. The mask image may be created and stored in, for example, a file in advance, or may be created by the mask information acquiring unit 206 based on the sensor information acquired by the sensor information acquiring unit 205. For example, the analysis unit 207 may create the mask image. Alternatively, an operator of the biological signal measurement system 1 may create the mask image by specifying the brain area in the sectional image displayed by the analysis display controller 202, on the screen.

Herein, a region of the brain on which the user focuses attention as an object to be analyzed is simply called the "brain area". Accordingly, the brain area does not necessarily include the whole region of the brain. For example, in the analysis of the brain activity, the cerebellum and the brain stem are excluded in some cases, and the region of the brain except these parts is called the "brain area" in some cases.

The analysis unit 207 is a functional unit for analyzing the sensor information (measured signals) acquired by the sensor information acquiring unit 205 and calculating signals representing the signal intensities (hereinafter, these signals are also called the "biological signals" in some cases) in various portions of the brain.

Specifically, the analysis unit 207 divides the brain area defined by the mask image into small areas (voxels), and estimates a degree of brain activity on a voxel-by-voxel basis (called "imaging of the brain activity"). For example, the signal intensities or degrees of changes in the signal intensities can be used as an indicator representing the degree of brain activity. Any method can be used for the imaging of the brain activity, and, for example, may only be a known technique, such as an approach called an adaptive beamformer or an approach using Bayesian factor analysis. The former approach has a higher resolution in the frequency direction than the latter approach, so that dimensions of the frequency increase in the imaging result of the brain activity.

In general, in the case of performing the imaging, a three-dimensional shape constituted by the mask image for the brain area is modeled as one or a plurality of spheres, and the inside of the model is calculated. This approach tends to cause an error in the modeling, such that the outside of the brain area is included or that a fine structure such as a cerebral sulcus is lost. So as not to lose a portion of the brain area, a larger area than the actual brain area is intentionally modeled in some cases.

The storage unit 208 is a functional unit for storing therein, for example, data of the biological signals representing the signal intensities calculated by the analysis unit 207. The storage unit 208 is implemented by the RAM 102 or the auxiliary storage device 104 illustrated in FIG. 2.

The information input unit 209 is a functional unit for receiving an operation for input of annotation information for appending related information as a comment to the sensor information, and for receiving various input operations to the time-frequency analysis screen 601. The information input unit 209 is implemented by the input device 106 illustrated in FIG. 2.

The collection display controller 201, the analysis display controller 202, the peak list controller 203, the sensor information acquiring unit 205, the mask information acquiring unit 206, and the analysis unit 207, which have been described above, are implemented by loading a computer program stored in, for example, the ROM 103, into the RAM 102, and executing the loaded computer program. One or some or all of the collection display controller 201, the analysis display controller 202, the peak list controller 203, the sensor information acquiring unit 205, the mask information acquiring unit 206, and the analysis unit 207 may be implemented not by the computer program as software, but by a hardware circuit, such as an application specific integrated circuit (ASIC) or a field-programmable gate array (FFGA).

The functional units illustrated in FIG. 3 are only for conceptually illustrating the functions thereof, and are not limited to being configured as illustrated in FIG. 3. For example, a plurality of functional units illustrated as independent functional units in FIG. 3 may be configured as one functional unit. In a converse manner, a function provided by one functional unit in FIG. 3 may be divided into a plurality of functions, and configured as a plurality of functional units.

Operation during Measurement Collection

Figure 4:
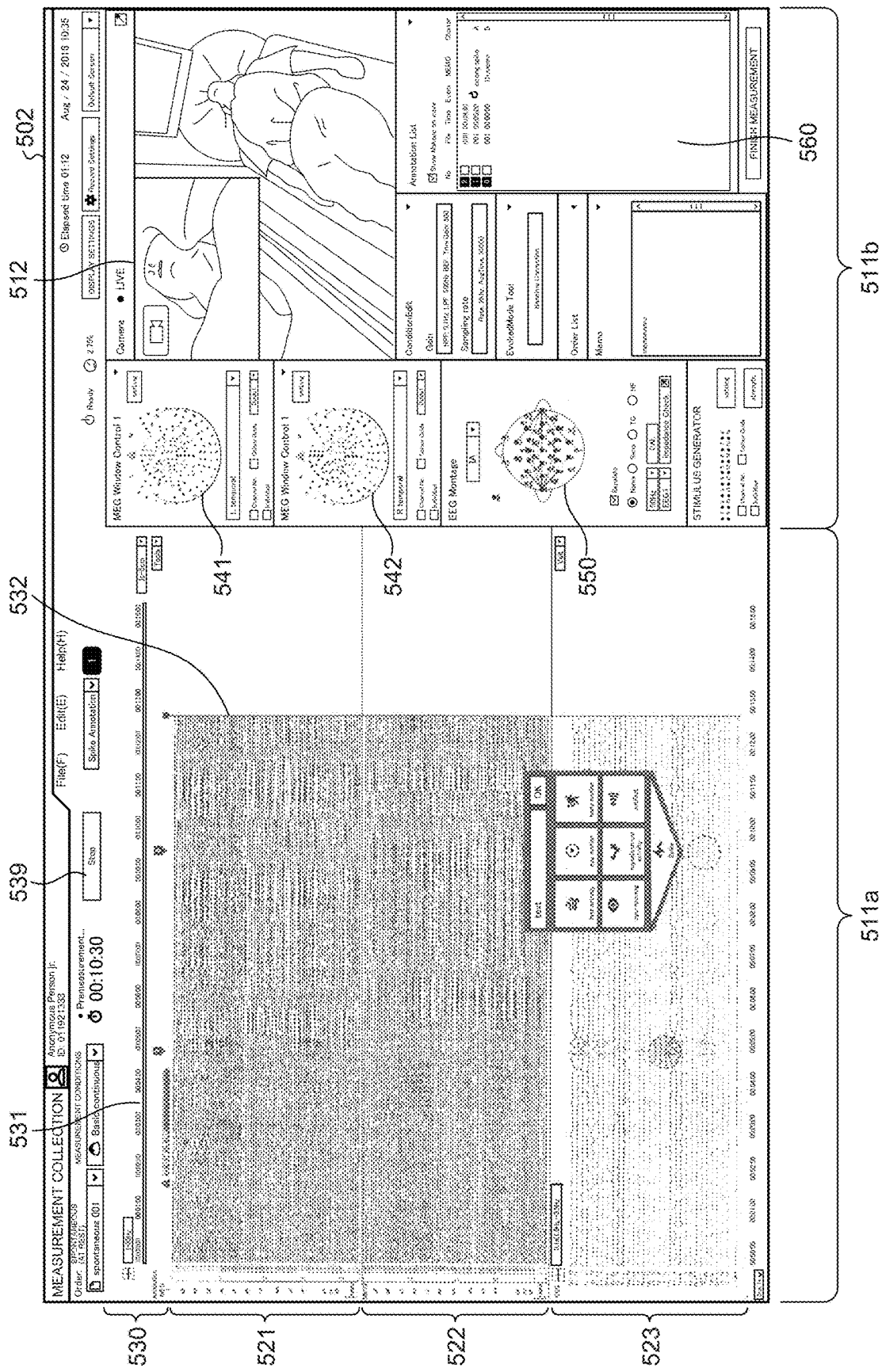
FIG. 4 is a view illustrating an example of a measurement collection screen.

FIG. 4 is a view illustrating an example of the measurement collection screen. As illustrated in FIG. 4, a measurement collection screen 502 includes an area 511a for displaying signal waveforms of the measured biological signals (herein, the MEG signals and the EEG signals) and an area 511b for displaying monitor information other than the signal waveforms.

The area 511b of the display screen displays a monitor window 512 for checking the state of the subject during the measurement. Displaying a live video of the subject during the measurement can increase reliability of checking and judgment of the signal waveforms. FIG. 4 illustrates a case where the entire measurement collection screen 502 is displayed on the display screen of one monitor display (display device 107). However, the left-side area 511a and the right-side area 511b may be separately displayed on two or more monitor displays.

The area 511a includes a first display area 530 for displaying time information on the signal detection in the horizontal direction of the screen and second display areas 521, 522, and 523 for displaying a plurality of signal waveforms based on the signal detection arranged in parallel in the vertical direction of the screen.

The area 511a displays a plurality of signal waveforms acquired from a plurality of sensors of the same type, or waveforms of a plurality of types of signals acquired from a group of a plurality of types of sensors, in synchronization with one another on an identical time axis 531. In the example illustrated in FIG. 4, the second display area 521 displays waveforms of a plurality of MEG signals obtained from the right side of the head of the subject, and the second display area 522 displays waveforms of a plurality of MEG signals obtained from the left side of the head of the subject, in parallel with one another. The second display area 523 displays waveforms of a plurality of EEG signals in parallel with one another. The EEG signal waveforms are voltage signals measured between the electrodes. The signal waveforms are displayed in association with respective identification numbers or channel numbers of the sensors from which the signals have been acquired.

After the measurement has started and measurement information has been collected from the sensors, the signal waveforms are displayed in the second display areas 521 to 523 of the area 511a rightward from the left ends thereof as time passes. A line 532 indicates the current time, and moves rightward from the left side of the screen. After the signal waveforms are displayed to the right end of the area 511a (right end of the time axis 531), the signal waveforms gradually disappear rightward from the left end of the screen, and new signal waveforms are sequentially displayed in the disappearing position rightward from the left side, and also the line 532 moves rightward from the left end. Along with this process, the first display area 530 extending in the horizontal direction displays a lapse of time on the time axis 531. The measurement collection is continued until an end button 539 is clicked.

The monitor window 512 of the area 511b displays the live video of the state of the subject lying on the table 4 with the head placed in the measuring device 3. The area 511b displays MEG distribution diagrams 541 and 542 and an EEG distribution diagram 550 corresponding to the signal waveforms in the second display areas 521, 522, and 523, respectively, and an annotation list 560. The annotation list 560 is a list of annotations marked on the signal waveforms of FIG. 4. Each time a position or a range on the signal waveforms is added in the second display areas 521 to 523, corresponding information is sequentially added to the annotation list 560.

If the end button 539 is selected (clicked) and the measurement is finished, highlighted portions specified in the second display areas 521 to 523 are stored in association with the signal waveforms. The annotation information displayed in the corresponding time position of the first display area 530 is also stored in association with an annotation number and time. Related information, such as the content of the annotation list 560, is also stored. By storing these pieces of display information, an analyst can easily recognize and analyze a problematic portion even if the analyst is a different person from a measurer.

Analysis Operation on Time-Frequency Analysis Screen

Figure 5:
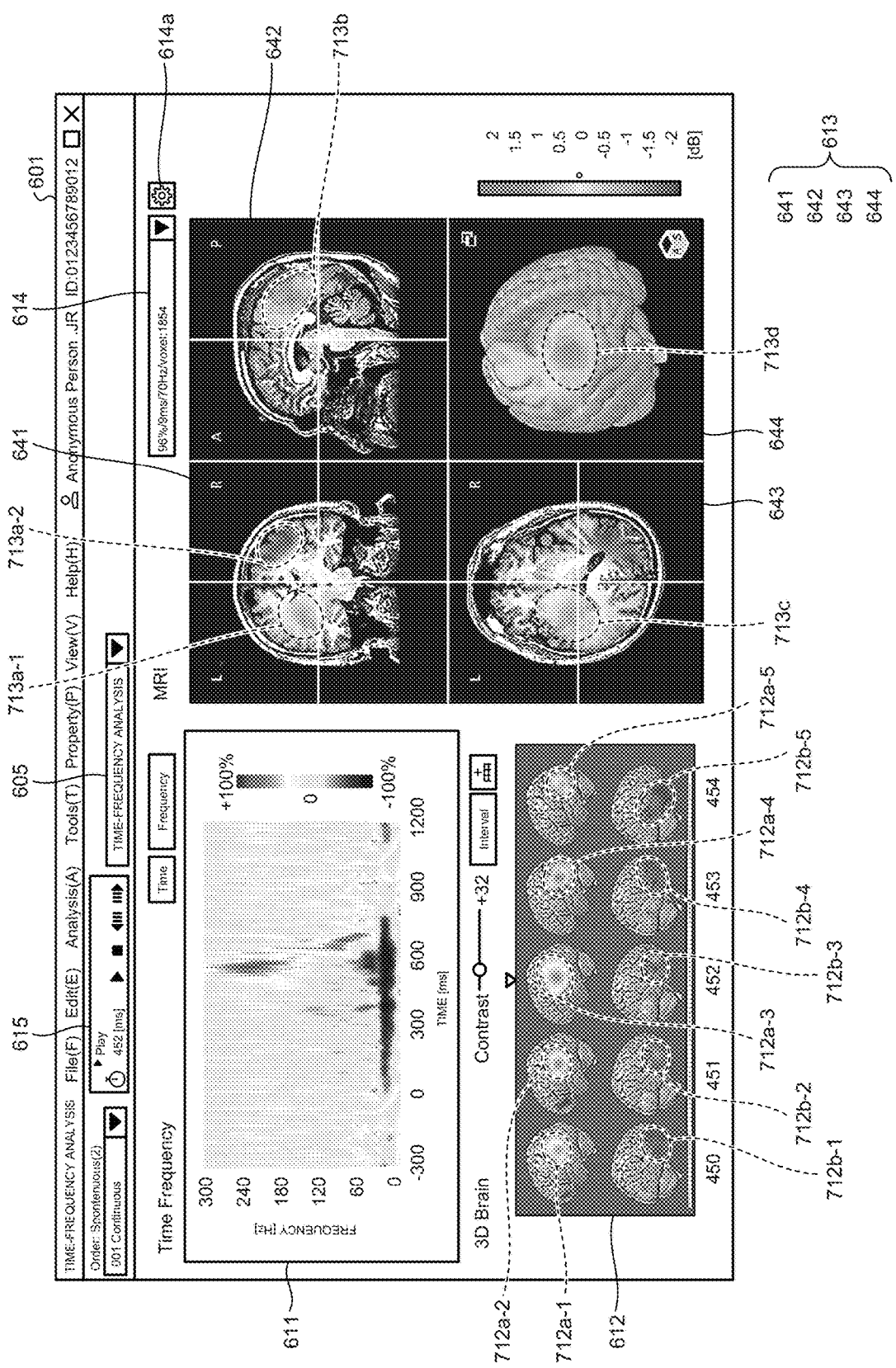
FIG. 5 is a view illustrating an example of a time-frequency analysis screen.

The following describes, using FIG. 5, an analysis operation on the time-frequency analysis screen 601 displayed on the information processing device 50. FIG. 5 is a view illustrating an example of the time-frequency analysis screen.

After an "analysis" button is clicked on an unillustrated start screen, the analysis unit 207 analyzes the sensor information (EEG signals or MEG signals) collected through the measurement collection operation, and calculates the biological signals representing the signal intensities in respective positions in the brain. Examples of a method for calculating the signal intensities include a spatial filter method, which is a known method. However, other methods may be used.

After the "analysis" button is clicked on the unillustrated start screen, the analysis display controller 202 displays the time-frequency analysis screen 601 illustrated in FIG. 5 on the display device 107. As illustrated in FIG. 5, the time-frequency analysis screen 601 displays an analysis screen switching list 605, the heat map 611, the stereoscopic view 612, the three-sided head view 613, the peak list 614, and the reproduction control panel 615.

A main purpose of the analysis and the measurement using the time-frequency analysis screen 601 is to identify and display regions vital to human life, such as the visual area, the auditory area, the somatosensory area, the motor area, and the language area. A peak list setting button 614*a* displayed on the right side of the peak list 614 is a button for displaying a window for setting conditions for peaks to be registered on the peak list 614. The function of the peak list setting button 614*a* will be described later. Details of display content and details of operations of the heat map 611, the stereoscopic view 612, the three-sided head view 613, the peak list 614, and the reproduction control panel 615 will be successively described later.

Peak List

Figure 6:
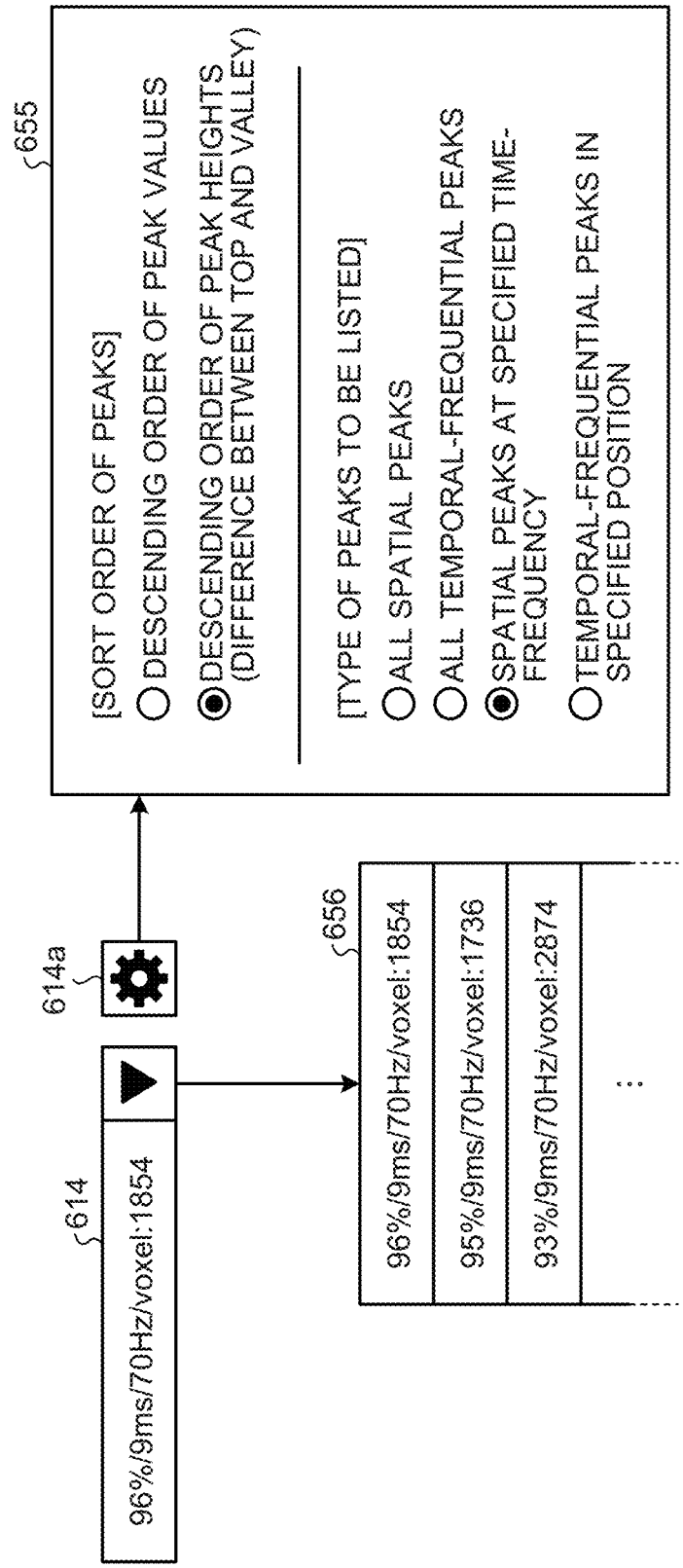
FIG. 6 is a diagram illustrating a setting example of a peak list.

The following describes the peak list, using FIG. 6. FIG. 6 is a diagram illustrating a setting example of the peak list.

The peak list 614 is a list on which the peaks of the signal intensities detected by the peak list controller 203 and satisfying the set conditions are registered. As illustrated in FIG. 6, if the peak list 614 is pulled down, the peak list controller 203 displays a pull-down list 656 serving as a list of the registered signal intensities.

The conditions for the peaks of the signal intensities detected by the peak list controller 203 can be set by clicking the peak list setting button 614*a*. Clicking the peak list setting button 614*a* causes the peak list controller 203 to display a dialog box 655 for setting the conditions for the detected peaks of the signal intensities.

The dialog box 655 first allows setting of how to sort the peak information registered on the peak list 614. If "descending order of peak values" is selected on the dialog box 655, the peak list controller 203 sorts the peak information registered on the peak list 614 in descending order of the signal intensities of the peaks. If, instead, "descending order of peak heights (difference between top and valley)" is selected on the dialog box 655, the peak list controller 203 sorts the peak information registered on the peak list 614 in descending order of differences between a signal intensity of a peak point and a signal intensity of a valley of the peak.

The dialog box 655 further allows setting of a type of the peak information registered on the peak list 614. If "all spatial peaks" is selected on the dialog box 655, the peak list controller 203 detects spatial peaks in the entire brain at respective times and frequencies in a time-frequency plane, and registers the detection results on the peak list 614. The term "spatial peaks" refers herein to peaks of the signal intensities of the biological signals in the entire brain at times and frequencies on which attention is focused.

If "all temporal-frequential peaks" is selected on the dialog box 655, the peak list controller 203 detects temporal-frequential peaks in the time-frequency plane in respective positions of the entire brain, and registers the detection results on the peak list 614. The term "temporal-frequential peaks" refers herein to peaks of the signal intensities of the biological signals in the time-frequency plane in positions of the brain on which attention is focused.

If "spatial peaks at specified time-frequency" is selected on the dialog box 655, the peak list controller 203 detects the spatial peaks in the entire brain at a time and a frequency specified in the time-frequency plane, and registers the detection results on the peak list 614. The specified time-frequency is not limited to one point, and may be selected as a range.

If "temporal-frequential peaks in specified position" is selected on the dialog box 655, the peak list controller 203 detects temporal-frequential peaks in the time-frequency plane in a specified position of the brain, and registers the detection results on the peak list 614. The specified position is not limited to one point, and may be selected as a range. For example, in a case of detecting peaks in the visual area, desired peaks are more likely to be detected by specifying the entire occipital region.

Heat Map

As illustrated in FIG. 5, the heat map 611 is a diagram obtained by performing time-frequency analysis on the biological signals representing the signal intensities in the respective positions in the brain calculated by the analysis unit 207, and by representing the time on the horizontal axis and the frequency on the vertical axis, and representing a distribution of the signal intensities of the biological signals identified by the time and the frequency using colors. In the example illustrated in FIG. 5, the signal intensities are represented by, for example, increase and decrease with respect to a predetermined reference. The predetermined reference is herein defined, for example, as follows: the average value of the signal intensity is 0% when no stimulus is applied to the subject. For example, if a certain stimulus is applied (for example, applying a physical shock, moving an arm, making an utterance, or hearing a sound) to the subject at time 0 ms, the heat map 611 represents an active state of the brain after the application of the stimulus at the subsequent time, and represents the active state of the brain before the application of the stimulus before time 0 ms. The display operation of the heat map 611 is controlled by the heat map display controller 211.

The analyst can perform a drag operation or a swipe operation on the information input unit 209 to specify a certain region on the heat map 611. The heat map display controller 211 displays, for example, a rectangular specified area 622-1 (refer to FIG. 7) having an area defined by, for example, the drag operation in the specified region. The specified area is displayed in any display form, such as a hollow rectangular region, a round shape, or a free shape.

If the certain region is specified on the heat map 611 as described above, the stereoscopic view 612 and the three-sided head view 613 display an average distribution of the signal intensities of the biological signals corresponding to the times and frequencies included in the specified region. Specifically, as illustrated in FIG. 5, the stereoscopic view 612 displays regions 712*a*-1 to 712*a*-5, and 712*b*-1 to 712*b*-5. The three-sided head view 613 displays regions 713*a*-1, 713*a*-2, 713*b*, 713*c*, and 713*d*.

Stereoscopic View

As illustrated in FIG. 5, the stereoscopic view 612 is a view that displays stereoscopic images (three-dimensional (3D) images) of the brain viewed from predetermined viewpoints. In the stereoscopic view 612, the signal intensities of the biological signals corresponding to positions (points or ranges) specified on the heat map 611 or positions of the peaks selected on the peak list 614 are displayed in a superimposed manner as the heat map. In the stereoscopic view 612, the stereoscopic images of the brain viewed from the same viewpoint are displayed in the same row. In the example illustrated in FIG. 5, stereoscopic views in the upper row of the stereoscopic view 612 are images of the left side of the brain, and stereoscopic views in the lower row thereof are images of the right side of the brain. The display operation of the stereoscopic view 612 is controlled by the stereoscopic display controller 212.

The stereoscopic view 612 illustrated in FIG. 5 is stereoscopic views of the brain viewed from two viewpoints, that is, stereoscopic views of the brain constituted by two rows. The stereoscopic view 612 is, however, not limited thereto, and may be displayed in another number of rows, or may have the number of rows that is changeable by setting. For example, when the language area of the brain is measured, since a right-left difference is important information, the stereoscopic views of the brain viewed from two viewpoints on the right and left sides of the brain only need to be displayed (displayed in two rows).

Three-Sided Head View

As illustrated in FIG. 5, the three-sided head view 613 is a three-directional sectional view (hereinafter, called "three-sided view" in some cases) in a certain position (point) of the brain. The three-sided head view 613 includes a sectional view 641 (coronal sectional view) representing a section orthogonal to the front-rear direction of the brain, a sectional view 642 (sagittal sectional view) representing a section orthogonal to the right-left direction of the brain, and a sectional view 643 (axial sectional view) representing a section orthogonal to the up-down direction of the brain. The three-sided head view 613 may include a stereoscopic image 644 serving as a 3D image.

Horizontally and vertically extending reference lines passing through the above-mentioned certain position (point) are drawn in the three-sided head view 613. The reference lines will be described later in detail (refer to FIG. 8). The display operation of the three-sided head view 613 is controlled by the section display controller 213.

Reproduction Control Panel

The reproduction control panel 615 is a user interface for the analyst to perform operation to reproduce and display states of the heat map 611, the stereoscopic view 612, and the three-sided head view 613 along with a lapse of time.

Figure 7:
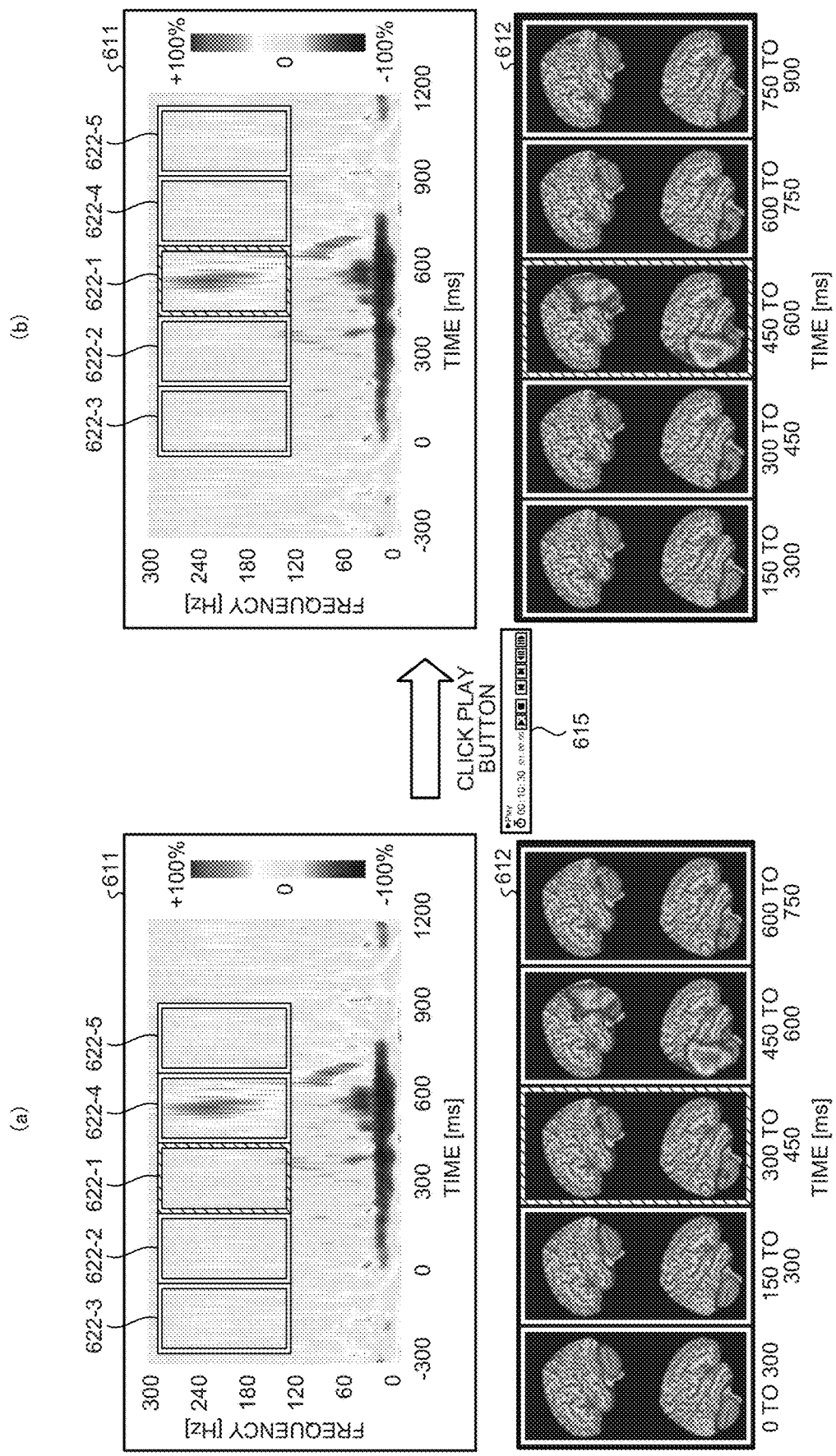
FIG. 7 is a diagram illustrating a state where a heat map and a stereoscopic view are reproduced and displayed by an operation on a reproduction control panel.

After the analyst clicks a "play" button on the reproduction control panel 615, the reproduction display controller 214 instructs the heat map display controller 211 to move the specified area 622-1 and corresponding areas 622-2 to 622-5 therearound in the rightward direction (direction in which time advances) along with the lapse of time, as illustrated in FIG. 7. The reproduction display controller 214 instructs the stereoscopic display controller 212 to switch the display of the stereoscopic views 612 corresponding to the respective areas along with the movement of the specified area 622-1 and the corresponding areas 622-2 to 622-5, as illustrated in FIG. 7. The reproduction display controller 214 instructs the section display controller 213 to display the heat map of the signal intensities corresponding to a time-frequency range corresponding to the moving specified area 622-1 in the three-sided head view 613 and the stereoscopic image 644 along with the movement of the specified area 622-1.

After the analyst clicks a "frame rewind" button on the reproduction control panel 615, the reproduction display controller 214 instructs the heat map display controller 211 to move the specified area 622-1 and the corresponding areas 622-2 to 622-5 therearound in the leftward direction (direction in which time travels back) by a predetermined period of time. The reproduction display controller 214 instructs the stereoscopic display controller 212 to switch the display of the stereoscopic views 612 corresponding to the respective areas along with the movement of the specified area 622-1 and the corresponding areas 622-2 to 622-5. The reproduction display controller 214 instructs the section display controller 213 to display the heat map of the signal intensities corresponding to the time-frequency range corresponding to the moved specified area 622-1 in the three-sided head view 613 and the stereoscopic image 644 along with the movement of the specified area 622-1.

Display Examples of Peak position

Figure 8:
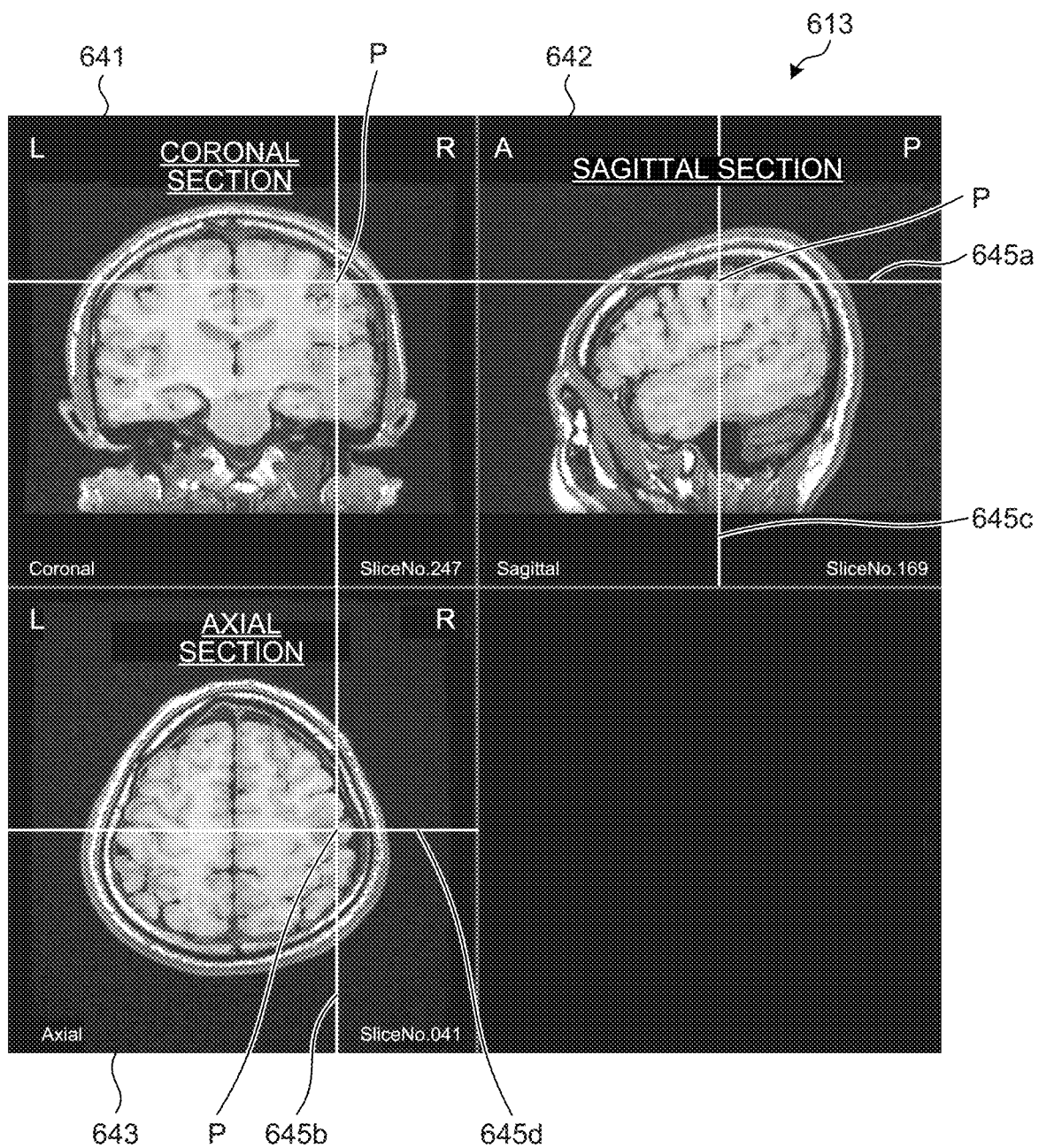
FIG. 8 is a view illustrating a display example of sectional images when a peak position is detected in a brain area.
Figure 9:
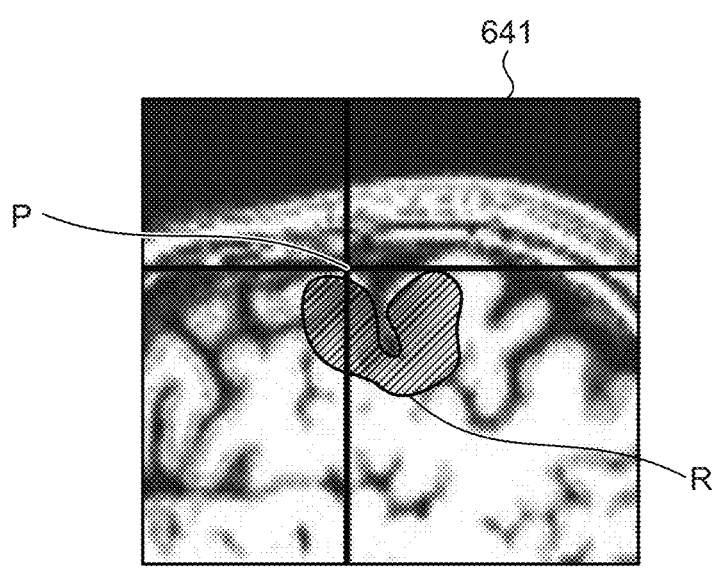
FIG. 9 is a view illustrating a display example of a sectional image when the peak position is detected outside the brain area.

The following describes display examples of the peak position of the signal intensities, using FIG. 8 and 9. FIG. 8 is a view illustrating a display example of the sectional images when the peak position is detected in the brain area. FIG. 9 is a view illustrating a display example of a sectional image when the peak position is detected outside the brain area.

The section display controller 213 selects one of the detected peak positions of the signal intensities based on a predetermined criterion, and displays the imaging results of the corresponding brain activity so as to be superimposed on the three-sided head view 613 (sectional images) corresponding to a selected peak position P. The peak position P is displayed as each intersection of crosses of the reference lines. If the peak position P is not detected, the user is notified accordingly, and sectional images to be used for display are selected according to a predetermined criterion (for example, selecting the center of the morphological image). The three-sided head view 613 preferably displays the coronal sectional view 641, the sagittal sectional view 642, and the axial sectional view 643 so as to be arranged as illustrated in FIG. 8.

Examples of the selection criterion of the peak position P include a method of selecting the peak position P in which the brain activity is most intense (the absolute value is the maximum), a method of selecting the peak position P residing closest to a pre-specified brain region, and a method of selecting the peak position P having the largest peak cluster size. The peak positions P may be presented as a list to the user, and display sectional images corresponding to one of the peak positions P selected by the user.

As illustrated in FIG. 8, a reference line 645*a* and a reference line 645*b* passing through the selected peak position P are drawn in the coronal sectional view 641. The reference line 645*a* and a reference line 645*c* passing through the selected peak position P are drawn in the sagittal sectional view 642. A reference line 645*d* and the reference line 645b passing through the selected peak position P are drawn in the axial sectional view 643.

If a spatial resolution of each of the sectional images differs from a spatial resolution of the imaging result of the brain activity and the peak position P does not correctly coincide with pixels of the sectional image, a sectional image may be selected that has the smallest distance from the peak position P, or a plurality of sectional images may be used to create an interpolated image and the created interpolated image may be substituted for the sectional image.

When each of the sectional images is displayed, the imaging result of the brain activity in a plane corresponding to the sectional image is preferably displayed in a superimposed manner, as illustrated in FIG. 8. When the superimposed display is performed, if the spatial resolution differs between the sectional image and the imaging result, one of the sectional image and the imaging result having the lower resolution is preferably interpolated as appropriate in accordance with the other of the sectional image and the imaging result having the higher resolution for display. Since the imaging result generally has a lower resolution, the imaging result is interpolated. A known method only needs to be used as a method for interpolation, and examples thereof include nearest interpolation, linear interpolation, and cubic interpolation.

The imaging result of the brain activity is preferably displayed so as to be capable of distinguishing the intensity of the brain activity using color and/or density, and is preferably settable in transmittance or opacity so as to allow reference to information on the sectional images when the imaging result is superimposed thereon.

FIG. 9 is the view illustrating the display example of the sectional image when the peak position is detected outside the brain area. In FIG. 9, a colored area R is a portion where the activity is intense in the brain area on which attention is focused, and the peak position P is preferably detected in the area R. However, at the time of modeling of the brain area performed in the process of the estimation of the brain activity, if the outside of the brain area is included or the fine structure such as the cerebral sulcus is lost, the brain activity may be estimated outside the actual brain area, and may be detected as the peak position P depending on the condition. In such a case, the user determines whether the measurement results are usable by viewing the sectional images on which the peak position P is displayed in a superimposed manner.

Flow of Processing to Display Peak Position in Superimposed Manner

The following describes, using FIG. 10, a flow of processing performed by the information processing device 50 to display the peak position P so as to be superimposed on the sectional images. FIG. 10 is a flowchart illustrating an example of the flow of the processing to display the peak position so as to be superimposed on the sectional images.

The mask information acquiring unit 206 reads the mask image (Step S11).

The analysis unit 207 analyzes the sensor information acquired by the sensor information acquiring unit 205, and calculates the biological signals. The analysis display controller 202 performs the imaging of the brain activity based on the calculated biological signals (Step S12).

The peak list controller 203 detects the peak position of the imaged biological signals (Step S13).

Furthermore, the peak list controller 203 determines whether the peak position P resides in the brain area (Step S14). If the peak position P is determined to be in the brain area (Yes at Step S14), processing at Step S15 is performed.

If the peak position P is determined not to be in the brain area (No at Step S14), processing at Step S17 is performed.

The peak list controller 203 compares the peak position P detected at Step S13 with the mask image for the brain area to determine whether the peak position P resides in the brain area. Examples of a method for determining whether the peak position P resides in the brain area include a method of employing a value of a pixel of the mask image closest to the peak position P and a method of determining that the peak position P is in the brain area only when four pixels of the mask image adjacent to the peak position P are all in the brain area.

If the determination at Step S14 is "Yes", the analysis display controller 202 (section display controller 213) displays the sectional images corresponding to the peak position P on the display device 107 (Step S15).

The analysis display controller 202 (section display controller 213) then displays the imaging results of the brain activity in the planes corresponding to the sectional images in a superimposed manner on the display device 107 (Step S16). Then, the information processing device 50 ends the series of processes illustrated in FIG. 10.

If the determination at Step S14 is "No", the analysis display controller 202 (section display controller 213) displays, on the display device 107, information for calling attention of the user to notify the user that the peak position P does not reside in the brain area (Step S17). Then, the processing at Step S15 is performed.

As described above, in the information processing device 50 (information display device) of the first embodiment, the mask information acquiring unit 206 acquires the mask information representing the area belonging to the brain in the morphological image (mask image acquiring step). Based on the mask information, the peak list controller 203 detects the peak position P (extremal value position) with the spatial extremal value in the brain activity information (extremal value detecting step). The section display controller 213 acquires the sectional images corresponding to the peak position P from the morphological image. The sensor information acquiring unit 205 acquires the brain activity distribution corresponding to the sectional images from the brain activity information. The section display controller 213 displays the brain activity distribution so as to be superimposed on each of the sectional images. Accordingly, the sectional images including the brain area can be appropriately displayed.

In the information processing device 50 (information display device) of the first embodiment, the mask information acquiring unit 206 acquires the mask information representing the area belonging to the brain in the morphological image. The peak list controller 203 detects the peak position P belonging to the area of the brain from among the identified peak positions with reference to the mask information. The section display controller 213 displays the detected peak position P so as to be superimposed on the brain activity distribution and each of the sectional images. Accordingly, the peak positions are first detected and then the peak position P residing in the brain area is detected to be used for the display. Therefore, peak positions other than the peak position P in the brain area are prevented from being selected.

In the information processing device 50 (information display device) of the first embodiment, the section display controller 213 further displays the peak position P (extremal value position) so as to be superimposed on the brain activity distribution and each of the sectional images. Accordingly, the peak position P can be displayed in an easily recognizable manner.

Modification of First Embodiment

In the first embodiment, the peak position P residing in the brain area is detected from among the peak positions detected at Step S13 (that is, those residing outside the brain area are excluded). In contrast, if the peak position P is determined to be residing outside the brain area at Step S14 of FIG. 10 (if Step S14 is determined to be "No"), another position may be substituted for the peak position P.

When the peak position P is detected from the imaging result of the brain activity, important information may be present at the periphery of the peak position P even if the peak position P resides outside the brain area. Therefore, attention may be focused on a peak cluster including the peak position P outside the brain area, and a position of another voxel included in the cluster and residing in the brain area may be substituted for the above-mentioned peak position P. The following methods can be exemplified as a method for selecting the voxel to be used as a substitute.

A first method is a method of selecting a voxel that resides on a boundary surface of the brain area and is closest to the peak position P.

A second method is a method of selecting a voxel that resides in the brain area including the boundary surface thereof, resides within a predetermined distance from the peak position P, and has a value nearest to that of the peak position P.

In other words, the analysis display controller 202 (section display controller 213) of the information processing device 50 can detect and display the substitute position for the peak position P by performing the processing to select the voxel using either of the above-described methods, Instead of performing the processing at Step S17 of FIG. 10.

As described above, in the information processing device 50 (information display device) according to the modification of the first embodiment, the peak list controller 203 detects the peak position P not belonging to the area of the brain from among the peak positions based on the peak positions and the mask information, and replaces the detected peak position P with the substitute position spatially close thereto. The section display controller 213 displays the substitute position for the peak position P so as to be superimposed on the brain activity distribution and each of the sectional images. Accordingly, even if the peak position P is detected outside the brain area, the information on the peak position P can be effectively used by substituting the neighboring position satisfying a predetermined criterion for the peak position P.

Second Embodiment

The following describes a second embodiment of an information display method, an information display device, an information display system, and a computer-readable medium according to the present invention in detail.

An information processing device 50a (not illustrated) of the second embodiment performs the imaging of the brain activity, and then removes information on the outside of the brain area from the imaging result so as to prevent the peak position P from being detected outside the brain area when the peak positions are detected.

The information processing device 50a has the same hardware configuration (FIG. 2) as that of the information processing device 50. The information processing device 50a has almost the same functional configuration (FIG. 3) as that of the information processing device 50, but only the section display controller 213 of the analysis display controller 202 has a different function from that of the first embodiment. In other words, the information processing device 50a includes an analysis display controller 202a. The analysis display controller 202a includes a section display controller 213a, instead of the section display controller 213 in the analysis display controller 202. The other component parts are the same as those of the first embodiment, and therefore, will be described using the same reference numerals.

In the second embodiment, the analysis display controller 202a (section display controller 213a) extracts only an imaging result present in the brain area from the imaging result of the brain activity, and thus updates the imaging result so as to prevent the peak positions outside the brain area from being detected during the detection of the peak positions at the next step.

As described above, the imaging of the brain activity is performed in a range wider than the actual brain area, and calculation in the imaging is performed voxel by voxel. Accordingly, the section display controller 213a refers to a pixel value of the mask image corresponding to coordinate values of each voxel, and determines whether the voxel resides inside or outside the brain area. Based on the result of this determination, the section display controller 213a may create an imaging result obtained by extracting only voxels present in the brain area, or may reduce values of voxels belonging to the outside of the brain area in the imaging result to prevent the peaks from being detected. The values of voxels can be reduced by replacing them with a value representing no brain activity, and for example, by only replacing pixel values stored as the imaging result with zero.

In the update of the imaging result described above, a selection of whether to extract only the voxels in the brain area or to restrain the voxels outside the brain area only needs to be performed according to a method for detecting the peak positions at the next step. In general, the voxels outside the brain area are preferably restrained, by which a data structure does not change.

Flow of Processing to Display Peak Position in Superimposed Manner

The following describes, using FIG. 11, a flow of processing performed by the information processing device 50a to display the peak position P so as to be superimposed on the sectional images. FIG. 11 is a flowchart illustrating an example of the flow of the processing to display the peak position so as to be superimposed on the sectional images in the second embodiment.

The information processing device 50a reads the mask image for the brain area (Step S21), and performs the imaging of the brain activity (Step S22). These processes have the same content as that of Steps S11 and S12 performed by the information processing device 50 in the first embodiment.

Then, the analysis display controller 202a (section display controller 213a) extracts an area corresponding to the brain area from the imaging result (Step S23). Specifically, as described above, the section display controller 213a refers to the pixel value of the mask image corresponding to the coordinate values of each voxel, and determines whether the voxel resides inside or outside the brain area.

Subsequently, the peak list controller 203 detects the peak position of the imaged biological signals (Step S24), and the section display controller 213*a* displays the sectional images corresponding to the peak position P on the display device 107 (Step S25). The section display controller 213*a* displays the imaging results of the brain activity in the planes corresponding to the sectional images in a superimposed manner on the display device 107 (Step S26). The above-described processes all have the same processing content as that of Steps S13, S15, and S16 described above performed by the information processing device 50.

As described above, the information processing device 50*a* (information display device) of the second embodiment removes the information not belonging to the area of the brain from the brain activity information based on the mask information, and identifies the peak position P (extremal value position) by executing the extremal value detecting step. Accordingly, the peak position P is not detected outside the brain area. Therefore, the peak position P need not be checked whether residing in the brain area. The second embodiment can obtain more peak positions than the first embodiment. In addition, the first embodiment excludes the peak position P residing outside the brain area. Therefore, if the peak cluster including the excluded peak position P overlaps the brain area, information on the cluster is not provided to the user. However, the second embodiment can remedy the problem because the peak position P is detected from the area overlapping the brain area.

Third Embodiment

The following describes a third embodiment of an information display method, an information display device, an information display system, and a computer-readable medium according to the present invention in detail.

When imaging the brain activity, an information processing device 50*b* (not illustrated) of the third embodiment prevents activities outside the brain area from being computationally estimated, and thereby, prevents the peak position P from being detected outside the brain area during the detection of the peak positions even without taking the measures exemplified in the first and second embodiments.

The information processing device 50*b* has the same hardware configuration (FIG. 2) as that of the information processing device 50. The information processing device 50*b* has almost the same functional configuration (FIG. 3) as that of the information processing device 50, but only the analysis unit 207 has a different function from that of the first embodiment. In other words, the information processing device 50*b* includes an analysis unit 207*a*. The other component parts are the same as those of the first embodiment, and therefore, will be described using the same reference numerals.

In the information processing device 50*b* of the third embodiment, the analysis unit 207*a* performs the imaging of the brain activity only in the brain area.

To estimate the spatial distribution of the brain activity based on brain magnetic field data measured using a magnetoencephalograph or brain wave data measured using an electroencephalograph, a spatial sensitivity distribution of sensors constituting devices that is called a lead field matrix needs to be calculated before calculating the brain activity (sensitivity of a certain sensor for a certain spatial position is simply called a lead field). In the calculation of the lead field matrix, the brain area is generally modeled as one or more spheres (an approach of modeling the brain area with one sphere is called "single-sphere model", and an approach of modeling the brain area with a plurality of spheres is called "multiple-sphere model" or "overlapping-sphere model"). As described above, to prevent the error in the modeling caused by tendencies, such as the inclusion of the outside of the brain area and the loss of a fine structure such as the cerebral sulcus, and to prevent the loss a portion of the brain area, a larger area than the actual brain area is modeled in some cases. Therefore, the lead field matrix is calculated such that the sensors also have sensitivity outside the brain area. As a result, using the lead field matrix may cause the brain activity to be also estimated outside the brain area.

Thus, the brain activity can be prevented from being estimated outside the brain area by configuring the lead field matrix such that sensors have sensitivity only in the brain area. The following methods can be exemplified as a specific method for achieving this object.

First, a method can be used in which lead fields outside the brain area are made invalid after the lead field matrix is calculated. This method is as follows: since the lead fields are normally calculated voxel by voxel, the lead fields are first calculated for all the voxels, and then, each of the voxels is determined whether residing inside or outside the brain area with reference to the mask image, and the lead fields for voxels residing outside the brain area are replaced with zero to be made invalid.

Second, a method can be used in which positions outside the brain area are excluded from targets of calculation in the calculation of the lead field matrix. In other words, this method is as follows: instead of calculating the lead fields for all the voxels as in the case of the first method, in the process of calculating the lead fields for the respective voxels, each voxel in question is sequentially checked whether residing inside or outside the brain area with reference to the mask image, and the lead fields are calculated for only the voxels present in the brain area so as to prevent the sensors from having sensitivity outside the brain area.

In the present embodiment, the analysis unit 207*a* performs the imaging of the brain activity based on either of the methods described above.

Flow of Processing to Display Peak Position in Superimposed Manner

The following describes, using FIG. 12, a flow of processing performed by the information processing device 50*b* to display the peak position P so as to be superimposed on the sectional images. FIG. 12 is a flowchart illustrating an example of the flow of the processing to display the peak position so as to be superimposed on the sectional images in the third embodiment.

The information processing device 50*b* reads the mask image for the brain area (Step S31). This processing has the same content as that of Step S11 performed by the information processing device 50 in the first embodiment.

Then, the analysis unit 207*a* uses either of the methods described above to analyze the sensor information acquired by the sensor information acquiring unit 205, and calculates the biological signals only in the brain area. The analysis display controller 202 performs the imaging of the brain activity only in the brain area (Step S32).

Subsequently, the peak list controller 203 detects the peak position of the imaged biological signals (Step S33), and the section display controller 213 displays the sectional images corresponding to the peak position P on the display device 107 (Step S34). The section display controller 213 displays the imaging results of the brain activity in the planes corresponding to the sectional images in a superimposed manner on the display device 107 (Step S35). The above-described processes all have the same processing content as that of Steps S13, S15, and SI6 described above performed by the information processing device 50.

As described above, in the information processing device 50b (information display device) according to a modification of the third embodiment, the analysis unit 207a calculates the brain activity information while excluding the positions not belonging to the area of the brain based on the mask information (brain activity information calculation step). Accordingly, the imaging results of the brain activity have values only in the brain area, so that the peak position P is not detected outside the brain area. Therefore, the peak position P need not be checked whether residing in the brain area.

An embodiment allows the sectional images including the brain area to be appropriately displayed.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information display method, the information display method comprising:
calculating brain activity information using at least one biological signal measured from a living body, the at least one biological signal including at least one of a magnetoencephalographic (MEG) signal, an electroencephalographic (EEG) signal, or a combination thereof;
acquiring mask information representing an area belonging to a brain in a morphological image including a plurality of sectional images;
detecting one or more extremal value positions with spatial extremal values in the brain activity information based on the mask information; and
displaying the brain activity information by superimposing the brain activity information on the morphological image including the plurality of sectional images, wherein
a sectional image corresponding to the one or more extremal value positions is acquired from the morphological image,
a brain activity distribution corresponding to the sectional image is acquired, and
the brain activity distribution is displayed so as to be superimposed on the sectional image.

2. The information display method according to claim 1, wherein
an extremal value position belonging to the area of the brain is detected from among the one or more extremal value positions based on the one or more extremal value positions and the mask information, and
the detected extremal value position is displayed so as to be superimposed on the brain activity distribution and the sectional image.

3. The information display method according to claim 2, wherein
the extremal value position belonging to the area of the brain is further detected from among the one or more extremal value positions based on a comparison of a magnitude of a value of the one or more extremal value positions and a desired threshold extremal value.

4. The information display method according to claim 1, wherein
an extremal value position not belonging to the area of the brain is detected from among the one or more extremal value positions based on the one or more extremal value positions and the mask information,
the detected extremal value position is replaced with a substitute position spatially close to the detected extremal value position, and
the substitute position is displayed so as to be superimposed on the brain activity distribution and the sectional image.

5. The information display method according to claim 1, wherein at the detecting the one or more extremal value positions, information not belonging to the area of the brain is removed from the brain activity information based on the mask information, and an extremal value position is identified.

6. The information display method according to claim 1, further comprising calculating the brain activity information using the at least one biological signal, wherein
at the calculating the brain activity information, a position not belonging to the area of the brain is excluded based on the mask information, to calculate the brain activity information.

7. The information display method according to claim 1, wherein the one or more extremal value positions are further displayed so as to be superimposed on the brain activity distribution and the sectional image.

8. The information display method according to claim 1, wherein
the morphological image is a magnetic resonance imaging (MRI) image.

9. The information display method according to claim 1, wherein
the mask information is an image including information for distinguishing the area belonging to the brain from other areas in the morphological image.

10. An information display device comprising:
at least one processor configured to,
calculate brain activity information using at least one biological signal measured from a living body, the at least one biological signal including at least one of a magnetoencephalographic (MEG) signal, an electroencephalographic (EEG) signal, or a combination thereof;
acquire mask information representing an area belonging to a brain in a morphological image including a plurality of sectional images;
detect one or more extremal value positions with spatial extremal values in the brain activity information based on the mask information; and
display the brain activity information by superimposing the brain activity information on the morphological image including the plurality of sectional images, the displaying including,
acquiring a sectional image corresponding to the one or more extremal value positions from the morphological image,
acquiring a brain activity distribution corresponding to the sectional image, and
displaying the brain activity distribution so as to be superimposed on the sectional image.

11. An information display system comprising:
at least one measuring device configured to measure at least one biological signal, the at least one biological signal including at least one of a magnetoencephalographic (MEG) signal, an electroencephalographic (EEG) signal, or a combination thereof; and
an information display device configured to display brain activity information calculated using the at least one biological signal measured by the measuring device so as to be superimposed on a morphological image including a plurality of sectional images, wherein
the information display system is configured to perform the information display method according to claim 1.

12. A non-transitory computer-readable medium including programmed instructions, that when executed, cause a computer to:
calculate brain activity information using at least one biological signal measured from a living body, the at least one biological signal including at least one of a magnetoencephalographic (MEG) signal, an electroencephalographic (EEG) signal, or a combination thereof;
acquire mask information representing an area belonging to a brain in a morphological image including a plurality of sectional images;
detect one or more extremal value positions with spatial extremal values in the brain activity information based on the mask information; and
display the brain activity information by superimposing the brain activity information on the morphological image including the plurality of sectional images, the displaying including,
acquiring a sectional image corresponding to the one or more extremal value positions from the morphological image,
acquiring a brain activity distribution corresponding to the sectional image, and
displaying the brain activity distribution so as to be superimposed on the sectional image.

13. The non-transitory computer-readable medium according to claim 12, wherein
an extremal value position belonging to the area of the brain is detected from among the one or more extremal value positions based on the one or more extremal value positions and the mask information, and
the detected extremal value position is displayed so as to be superimposed on the brain activity distribution and the sectional image.

14. The non-transitory computer-readable medium according to claim 13, wherein
the extremal value position belonging to the area of the brain is further detected from among the one or more extremal value positions based on a comparison of a magnitude of a value of the one or more extremal value positions and a desired threshold extremal value.

15. The non-transitory computer-readable medium according to claim 12, wherein
an extremal value position not belonging to the area of the brain is detected from among the one or more extremal value positions based on the one or more extremal value positions and the mask information,
the detected extremal value position is replaced with a substitute position spatially close to the detected extremal value position, and
the substitute position is displayed so as to be superimposed on the brain activity distribution and the sectional image.

16. The non-transitory computer-readable medium according to claim 12, wherein at the detecting the one or more extremal value positions, information not belonging to the area of the brain is removed from the brain activity information based on the mask information, and an extremal value position is identified.

17. The non-transitory computer-readable medium according to claim 12, wherein the computer is further caused to:
calculate the brain activity information using the at least one biological signal, wherein
at the calculating the brain activity information, a position not belonging to the area of the brain is excluded based on the mask information, to calculate the brain activity information.

18. The non-transitory computer-readable medium according to claim 12, wherein the one or more extremal value positions are further displayed so as to be superimposed on the brain activity distribution and the sectional image.

19. The non-transitory computer-readable medium according to claim 12, wherein the morphological image is a magnetic resonance imaging (MRI) image.

20. The non-transitory computer-readable medium according to claim 12, wherein
the mask information is an image including information for distinguishing the area belonging to the brain from other areas in the morphological image.

* * * * *